United States Patent [19]

Bunczk et al.

[11] Patent Number: 4,911,859
[45] Date of Patent: Mar. 27, 1990

[54] TOILET BOWL CLEANERS CONTAINING IODOPHORS

[75] Inventors: Charles J. Bunczk, Norristown; Peter A. Burke, Downingtown; William R. Camp, Pennside, all of Pa.

[73] Assignee: Kiwi Brands, Inc., Douglasville, Pa.

[21] Appl. No.: 244,735

[22] Filed: Sep. 15, 1988

[51] Int. Cl.$^4$ .................. C11D 3/04; C11D 3/20; C11D 3/22; C11D 17/00

[52] U.S. Cl. .................. 252/106; 252/89.1; 252/174; 252/174.17; 252/174.21; 252/174.22; 252/DIG. 16; 134/42; 4/227; 4/228

[58] Field of Search ............... 252/89.1, 90, 106, 134, 252/174, 174.21:174.22, 174.17, 170, DIG. 16; 134/42

[56] References Cited

U.S. PATENT DOCUMENTS

| | | | |
|---|---|---|---|
| 3,504,384 | 4/1970 | Radley et al. | 4/228 |
| 4,043,931 | 8/1977 | Jeffrey et al. | 252/93 |
| 4,278,571 | 7/1981 | Choy | 252/89 |
| 4,308,625 | 1/1982 | Kitko | 4/228 |
| 4,310,434 | 1/1982 | Choy | 252/174.21 |
| 4,396,522 | 8/1983 | Callicott et al. | 252/163 |
| 4,477,363 | 10/1984 | Wong et al. | 252/134 |
| 4,722,801 | 2/1988 | Bunczk et al. | 252/106 |
| 4,792,445 | 12/1988 | Rivera | 252/106 |

OTHER PUBLICATIONS

D. H. Terry & H. A. Shelanski, "Iodine As a Germicide" pp. 69–73 (approx 1952).

*Primary Examiner*—Paul Lieberman
*Assistant Examiner*—John F. Nally
*Attorney, Agent, or Firm*—Steele, Gould & Fried

[57] ABSTRACT

Solid cake lavoratory cleansing block composition comprising an iodophor, polyethylene oxide polymer having a molecular weight between about 1 to 6 million, a dye, calcium sulfate and optional ingredients which include fragrances, binders, filler material and mixtures thereof.

18 Claims, No Drawings

TOILET BOWL CLEANERS CONTAINING IODOPHORS

FIELD OF THE INVENTION

The present invention relates to cake compositions which are useful for the treatment of the flush water of toilets. More particularly, the invention is concerned with a long lasting iodophor-containing toilet tank dispenser which provides improved cleaning, a sanitizing action and is responsive to tee flushing of the toilet.

BACKGROUND OF THE INVENTION

In treating toilet flush water with chemicals in order to produce desirable effects such as bowl aesthetics, cleaning, disinfection, deodorization, aerosol reduction, etc., it is desirable that the chemicals be dispensed into the flush water automatically each time the toilet is flushed. The prior art discloses numerous devices which have been designed for this purpose.

Particularly desirable devices are those comprising a solid cake composition. In this type of device, a measured amount of water enters the device during one flush cycle and remains in contact with the cake between flushes, thereby forming a concentrated solution of the composition which is dispensed into the flush water during the next flush. The advantages of such devices are that the chemical composition can be packaged and shipped in more concentrated form than aqueous solutions of tee chemicals. Also, the problems of liquid spillage resulting from breakage of the dispensers during shipment or handling is eliminated.

Prior art surfactant cake compositions are disclosed in U.S. Pat. No. 4,308,625, Kitko, issued Jan. 5, 1982, and U.S. Pat. No. 4,043,931, Jeffrey et al, issued Aug. 23, 1977. These patents disclose a lavoratory cleansing tablet which is formed with two or more nonionic surfactants which includes the of polyalkoxylated alcohols. U.S. Pat. No. 4,477,363, Wong et al, issue Oct. 16, 1984, discloses a solid cake comprising free fatty alcohol and a buffered alkali earth metal alkyl sulfate surfactant. U.S. Pat. No. 4,310,434, Choy et al, issued Jan. 12, 1982; and U.S. Pat. No. 4,278,571, Choy, issued July 14, 1981, entitled "Surfactant Cake Compositions"; all of which are incorporated herein by reference, disclose surfactant cake compositions containing dyes and perfumes which are utilized in the present invention. The surfactants provide cleaning and sudsing in the toilet bowl and also serve to dispense other components of the compositions such as dyes, perfumes, organic resins, etc.

Water-soluble inert salts such as alkali metal chlorides and sulfates are used in such compositions to act as a "filler" so that the composition can be formed int cakes of desirable size without using excessive amounts of active ingredients. The predominant ingredients of the cake compositions are usually the surfactant, perfume and the filler salt.

Automatically dispensed toilet bowl cleaning and/or sanitizing products, which contain dyes to provide a visual signal to the user that the product is being dispensed, are well known. Such products are sold in the United States under the brand names VANISH AUTOMATIC (Drackett Products), TY-D-BOL AUTOMATIC (Kiwi Brands, Inc.) and SANIFLUSH AUTOMATIC (Boyle-Midway). None of these products contains an iodophor sanitizing agent and all of them provide a color to the bowl water which persists between flushings. U.S. Pat. No. 3,504,384, Radleyy et al, issued Apr. 7, 1970, discloses a dual compartment dispenser for automatically dispensing a hypochlorite solution and a surfactant/dye solution to the toilet bowl during flushing. The dye which is taught in the patent is Disulfide Blue VN150. This dye is resistant to oxidation to a colorless state by hypochlorite; thus, it provides a persistent color to the toilet bowl water, even in the presence of the hypochlorite.

In order to meet the Environmental Protection Agency efficacy data requirements for in-tank sanitizer products claims for effectiveness, it is necessary that the user be able to determine the product effectiveness. That is, the color indicator must show that the sanitizing ingredient is still present in a sanitizing amount. Consequently, it is essential that the sanitizing agent have the same life in the sanitizing product as the color indicator.

The use of chlorine or hypochlorite ion as the sanitizing agent has the disadvantage that most dyes are oxidized to a colorless state and there is no visual indication that the sanitizing agent is active and working in the toilet bowl.

The use of iodine-containing formulations have been previously considered as sanitizing agents for toilets because of their greater sanitizing capabilities than chlorine-containing agents. However, the iodine-containing agents have not been previously employed in cake toilet compositions because they yield an unacceptable color in the toilet bowl. Also, prior to the present invention there has not been provided a means for providing a controlled release of iodine so that the iodine and dye will last for the life of the cleansing block. The most effective means to provide the iodine is through use of a germicidal complex of iodine with a copolymer which is commonly identified as an iodophor.

It is an object of the present invention to provide a solid cake composition containing iodophors which are suitable for use for automatically dispensing cleaning agents into the toilet.

It is a further object of the present invention to provide a means for intensifying the sanitizing effect of the iodine released in iodophor-containing lavoratory cleansing blocks.

It is a still further object of the present invention to provide a lavoratory block which has a long and uniform block life that provides a controlled release of iodophor.

It is a yet still further object of the present invention to provide an iodophor-containing lavoratory block which releases a dye and iodophor for substantially the same period of time.

Other objects, advantages and novel features of the present invention will be apparent to those skilled in the art from the following description and appended claims.

SUMMARY OF THE INVENTION

The objectives of the invention are achieved by providing a solid cake composition which comprises an iodophor, a polyethylene oxide polymer having a molecular weight from about 1 to about 6 million, a dye, calcium sulfate, and optional ingredients selected from the groups consisting of fragrances, binders, filler material and mixtures thereof.

The type of iodophor utilized is not critical to the present invention but the amount of iodophor used must contain an amount of iodine calculated as elemental iodine to comprise about at least 1% preferably, between about 1 to about 6% by weight of composition. However, a greater amount may be utilized but is not necessary for achieving the objects of the invention.

It is also advantageous that the ratio of iodophor calculated as elemental iodine to dye be about 2.5:10 preferably 3.5:5 so as to result in a life of the iodophor in the composition being substantially the same as that of the dye.

It is understood that a greater amount of iodophor may be present. However, a suitable commercial product having an in-tank life of about 30 days needs only up to about 6% of iodophor calculated as elemental iodine. The greater amount only increases the cost of the cleansing block.

The calcium sulfate utilized may be either the dihydrate or anhydrous form. Preferably, the two forms are utilized. However, when only the dihydrate form is utilized, it is advantageous that tee polyethylene oxide polymer be present in an amount of at least 6%. Calcium sulfate also serves as an adsorbing agent for the iodophor and as a determinant for controlling solubility.

It has all been found that the use of up to about 5% by weight of composition of citric acid, tartaric acid or a free acid form of a phosphonate compound produces a greater intensification of the sanitizing effect of the iodophor.

DESCRIPTION OF THE PREFERRED EMBODIMENTS

According to one embodiment of the invention, a toilet cake composition is provided in tablet form having an in-tank life of about 30 days which comprises an amount of iodophor containing an amount of iodine calculated as elemental iodine to comprise preferably about 1% to 6% by weight of composition, about 2 to 20% by weight of composition, preferably about 5 to 10% by weight of a polyethylene oxide homopolymer having a molecular weight between about 1 to 6 million, about 1 to 75% by weight of composition of calcium sulfate, about 1 to 10% by weight of composition of dye, and the remainder f the ingredients comprising optional ingredients selected from the group consisting of surfactants, fragrances, fillers, binders, extenders and the like.

A suitable composition for forming a tablet by the compression method comprises an amount of iodophor containing an amount of iodine calculated as elemental iodine to comprise about 1% to 6% by weight of composition, about 40-60% by weight of calcium sulfate dihydrate, about 2.0-30% by weight calcium sulfate anhydrous, about 2-20% by weight polyethylene oxide homopolymer having a molecular weight between 1-6 million, preferably as a mixture of high and low molecular weights, about 0-20% by weight binder, about 2-10% by weight fillers including optionally, plasticizers, fragrances and perfumes. It is also advantageous to include up to about 5.0% by weight of a flow control agent and/or absorber for powders, for example, fumed silica.

Suitable binders which may be utilized include ethylene oxide/propylene oxide copolymers, guar gum, polyvinyl pyrrolidone, hydroxyethylene cellulose, PEG 8000, polyethylene glycol, and the like.

For the tablets which are to be prepared by extrusion, about 10-25% by weight of extrusion aids may be added, for example anionic alkalyds such as sodium dodecylbenzene sulfonate.

Preferably, the amount of iodophor placed n the composition should be chosen so as to last at least as long as (i.e., through at least as many flushes as) the amount of dye composition in the dye composition dispensing means. When the consumer no longer sees any color appear in the bowl when flushing the toilet, this indicates that it is time to replace the system (dye and sanitizer). It is desirable to have a persistent color in the toilet bowl between flushes, and, therefore, it is preferable that the supply of sanitizer last for at least as long as the supply of dye.

Various optional materials may be included in the compositions herein.

Dyes may be included at levels of from about 1.0 to 10.0% by weight. Examples of suitable dyes are Alizarine Light Blue B (C.I. 63010), Carta Blue VP (C.I. 24401), Acid Green 2G (C.I. 42085), Astragon Green D (C.I. 42040) Supranol Cyanine 7B (C.I. 42675), Maxilon Blue 3RL (C.I. Basic Blue 80), acid yellow 23, acid violet 17, a direct violet dye (direct violet 51), Drimarine Blue Z-RL (C.I. Reactive Blue 18), Alizarine Light Blue H-RL (C.I. Acid Blue 182), FD&C Blue No. 1, FD&C Green No. 3 and Acid Blue No. 9. Others are disclosed in the aforementioned U.S. Pat. Nos. 4,310,434 and 4,477,363, which are herewith incorporated by reference.

The cakes may also contain perfumes to impart an acceptable odor to the flushing water. The perfume may be in solid form and is suitably present in an amount up to 10% by weight. In this connection, it may be noted that the term "perfume" is intended to refer to any material giving an acceptable odor and thus materials giving a "disinfectant" odor such as essential oils, pine extracts, terpinolenes, ortho phenyl phenol or paradichlorobenzene may be employed. The essential oils and pine extracts also contribute as plasticizers and are functional to a degree in extending block life. Other suitable perfumes or fragrances are disclosed in U.S. Pat. No. 4,396,522 of Callicott et al, which is herein incorporated by reference.

The cake formulation may also contain other binding and/or plasticizing ingredients serving to assist in the manufacture thereof, for example, polypropylene glycol having a molecular weight from about 300 to about 10,000 in an amount up to about 20% by weight, preferably about 4% to about 15% by weight of the mixture may be used. The polypropylene glycol reduces the melt viscosity, acts as a demolding agent and also acts to plasticize the block when the composition is prepared by a casting process. Other suitable plasticizers such as pine oil fractions, d-limonene, dipentene and the ethylene oxide-propylene oxide block copolymers may be utilized.

The blocks of the present invention can be produced by a variety of processes, e.g., casting/moulding process, by tablet compression process or by an extrusion process, all of which are well known in the art. The table compression process is the preferred process of the invention.

If desired, other halophor may be added, for example, bromophors such as dibromopropamidine isethionate (sold under the trademark BRULIDINE), 2-bromo-2-nitropropane-1, 3-diol (sold under the trademark BRONOPOL), bromochlorodimethyl hydantoin, dibromodimethyl hydantoin, and 2-cyano-2,2-dibromo acetamide, preferably in an amount up to about 5% by weight.

In order that the invention may be better understood the following examples are given by way of illustration only. In the examples, all parts and percentages are by weight of composition unless otherwise stated.

The following examples are for compositions suited for forming shaped bodies of blocks of the invention.

EXAMPLE 1

A solid compacted sanitizing composition cake was prepared by dry-mixing the following ingredients and then subjecting the mixture to a compaction pressure of about 2.5 tons per square inch of a Manesty RS3 Tablet Press:

|  | % |
|---|---|
| Calcium Sulfate Dihydrate | 59.8 |
| Calcium Sulfate Anhydrous | 10.0 |
| Fumed Silica | 4.0 |
| Iodophor (Biopal NR-20) | 8.5 |
| Polyvinyl Pyrrolidone Iodine Complex (Povidone) | 5.7 |
| Dye (Acid Blue #9) | 5.0 |
| Polyethylene oxide polymer (Polyox 60K) | 2.0 |
| Polyethylene glycol (PEG 4500) | 5.0 |
|  | 100.0 |

The resulting tablet had an in-tank life of about 30 days and met the EPA requirements till the end of the period of maintaining a sanitizing effect while dispersing dye.

EXAMPLE 2

Following the procedure of Example 1, a cleansing block is formed with the following composition.

|  | % |
|---|---|
| Calcium Sulfate Coarse Dihydrate | 49.0 |
| Calcium Sulfate Anhydrous | 10.0 |
| Povidone | 21.0 |
| Polyox Coagulant | 5.0 |
| Acid Blue #9 | 5.0 |
| EO/PO Block Copolymer F108 | 10.0 |
|  | 100.0 |

If desired, in place of a portion of the calcium sulfate there may be added a fragrance.

EXAMPLE 3

Following the procedure of Example 1, a cleansing block is formed with the following composition.

|  | % |
|---|---|
| Calcium Sulfate Fine Dihydrate | 48.0 |
| Calcium Sulfate Fine Anhydrous | 25.8 |
| Fumed Silica | 5.0 |
| Biopal | 8.5 |
| Povidone | 5.7 |
| Acid Blue #9 | 5.0 |
| Polyox Coagulant | 2.0 |
|  | 100.0 |

If desired, in place of a portion of the calcium sulfate, there may be added fragrances and citric acid.

EXAMPLE 4

Following the procedure of Example 1 a cleansing block is prepared from the following composition:

|  | % |
|---|---|
| Calcium Sulfate, dihydrate (fine) | 60.45 |
| Calcium Sulfate, anhydrous (fine) | 4.51 |
| Aerosil 380 | 3.97 |
| Biopal | 11.07 |
| PVP-I2 | 4.00 |
| Acid Blue #9 | 5.00 |
| Polyox, coagulant | 2.00 |
| Polyethylene Glycol E4500 | 4.00 |
| Sodium Dodecyl Benzene Sulfonate | 5.00 |
|  | 100.00 |

The formula provides a cleansing block having good anti-bacterial properties.

In lieu of sodium dodecyl benzene sulfonate there may be utilized in its place a similar amount of sodium alpha olefin ($C_{14}$–$C_{16}$) sulfonate or oleyl/palmitic succinate amide, or the like.

The principals, preferred embodiments and modes of operation of the present invention have been described in the foregoing specification. The invention which is intended to be protected herein, however, is not to be constructed as limited to particular forms disclosed, since these are to be regarded as illustrative rather than restrictive. Variations and changes may be made by those skilled in the art without departing from the spirit of the invention.

What is claimed is:

1. A solid cake lavoratory cleansing and sanitizing block composition which indicates the presence of a sanitizing agent comprising from about 2% to about 20% by weight of composition of polyethylene oxide polymer having a molecular weight from about 1 million to about 6 million, a sanitizing agent which is an iodophor in an amount containing iodine calculated as elemental iodine to comprise at least about 1% by weight of composition, about 1% to about 10% by weight of composition of dye, the ratio of iodophor to dye being in an amount whereby the life of the iodophor to dye being in an amount whereby the life of the iodophor in the composition is substantially the same as the dye and the presence of the dye indicates the presence of the iodophor, about 1% to about 75% by weight of composition of calcium sulfate, and the remainder being ingredients selected from the group consisting of fragrances, binder, filler material and mixtures thereof.

2. The cleansing block composition of claim 1 including an amount of up to about 20% by weight of composition of a binding agent which is selected from the group consisting of guar gum, hydroxyethyl cellulose, ethylene oxide/propylene oxide copolymer and polyvinyl pyrrolidone.

3. The cleansing block composition of claim 1 including a powder flow aid.

4. The cleansing block composition of claim 3 wherein said flow aid is fumed silica.

5. The cleansing block composition of claim 1 wherein said polyethylene oxide polymer comprises a mixture of polymers of different molecular weights.

6. The cleansing block composition of claim 1 wherein said calcium sulfate is a mixture of calcium sulfate dihydrate and calcium sulfate anhydrous.

7. The cleansing block composition of claim 1 wherein the ratio of iodophor calculated as elemental iodine to dye is about 3.5:5.

8. The cleansing block composition of claim 1 including a bromophor.

9. A solid cake lavoratory cleansing and sanitizing block composition which indicates the presence of a sanitizing agent comprising about 40% to 60% by weight calcium sulfate dihydrate, about 2.0% to about 30% by weight calcium sulfate anhydrous, about 2% to 20% by weight polyethylene oxide homopolymer having a molecular weight between about 1 million to 6 million, about 1% to about 10% by weight of dye, a sanitizing agent which is an iodophor in an amount containing iodine calculated as elemental iodine to comprise about 1% to about 6% by weight of composition, the ratio of iodophor to dye being in an amount whereby the life of the iodophor is substantially the same as the dye and the presence of the dye indicates the presence of the iodophor about 0 to 20% by weight binder, and about 2% to about 10% by weight of filler material.

10. The cleansing block composition of claim 9 including about 0 to 5% by weight of fumed silica.

11. The cleansing block composition of claim 9 wherein said polyethylene oxide polymer comprises a mixture of polymers having a molecular weight between 1 and 4 million with polymers having a molecular weight from 4 to 6 million.

12. The cleansing block composition of claim 9 wherein the ratio of iodophor calculated as elemental iodine to dye is about 3.5:5.

13. The cleansing block composition of claim 9 including a member selected from the group consisting of citric acid, tartaric acid and a free acid form of a phosphate compound for intensifying the sanitizing effect of the iodophor.

14. The cleansing block composition of claim 9 wherein said binder is selected from the group consisting of ethylene oxide/propylene oxide block copolymer, guar gum, polyvinyl pyrrolidone, hydroxyethyl cellulose and poyethylene glycol.

15. The cleansing block of claim 9 including an extrusion aid.

16. The cleansing block of claim 9 including a further halophor.

17. The cleansing block of claim 16 wherein said further halophor is a bromophor.

18. The cleansing block of claim 17 wherein said bromophor is selected from the group of bromochlorodimethyl hydantoin, dibromodimethyl hydantoin and 2-cyano-2,2-dibromo acetamide, dibromopropamidine isethionate and 2-bromo-2-nitropropane-1, 3-diol.

* * * * *